United States Patent [19]
Larson et al.

[11] Patent Number: 5,990,476
[45] Date of Patent: Nov. 23, 1999

[54] CONTROL OF SURFACE POTENTIAL OF INSULATING SPECIMENS IN SURFACE ANALYSIS

[75] Inventors: Paul E. Larson, Bloomington, Minn.; Michael A. Kelly, Portola Valley, Calif.

[73] Assignee: Physical Electronics Inc, Eden Prairie, Minn.

[21] Appl. No.: 08/968,454

[22] Filed: Nov. 12, 1997

Related U.S. Application Data

[60] Provisional application No. 60/033,609, Dec. 17, 1996.

[51] Int. Cl.$^6$ ............................... H05H 3/00; H01J 37/26
[52] U.S. Cl. ........................ 250/251; 250/310; 250/305
[58] Field of Search ................................... 250/305, 309, 250/310, 251

[56] References Cited

U.S. PATENT DOCUMENTS

| | | | |
|---|---|---|---|
| 4,052,614 | 10/1977 | Grunthaner et al. | 250/310 |
| 4,639,301 | 1/1987 | Doherty et al. | |
| 4,680,467 | 7/1987 | Bryson et al. | 250/305 |
| 4,939,360 | 7/1990 | Sakai | 250/251 |
| 5,034,605 | 7/1991 | Bayly | 250/309 |
| 5,315,113 | 5/1994 | Larson et al. | 250/305 |
| 5,432,345 | 7/1995 | Kelly | 250/306 |
| 5,444,242 | 8/1995 | Larson et al. | 250/305 |

OTHER PUBLICATIONS

K. Wittmaack, "Primary–ion Charge Compensation in SIMS Analysis of Insulators", J. Appl. Phys. 50 (1) (Jan. 1979).

P. E. Larson and M. A. Kelly, "Surface Charge Neutralization of Insulating Samples in X–Ray Photoemission Spectroscopy", J. Vac. Sci. Technol. A 16 (6), 3483–3489 (Nov./Dec. 1998).

*Primary Examiner*—Bruce C. Anderson
*Attorney, Agent, or Firm*—H. S. Ingham

[57] ABSTRACT

An apparatus effects a uniform surface potential on an insulating specimen in an x-ray photoelectron or a secondary ion emission instrument in which there is positive charging of an irradiation region. An area of the specimen including the irradiation region is flooded with a beam of low energy electrons to neutralize the positive charging, causing negative charging of the flooding area. Positive ions are directed onto the flooding area to neutralize the negative charging. The electron beam has an energy less than about 2 eV and an energy spread less than about 0.5 eV. The ratio of the beam distance to its diameter is less than about 10. The ions have an energy less than 10 eV.

20 Claims, 3 Drawing Sheets

CONTROL OF SURFACE POTENTIAL OF INSULATING SPECIMENS IN SURFACE ANALYSIS

This application claims the benefit of copending provisional application Ser. No. 60/033,609. This invention relates generally to analysis of surfaces, particularly to electron and ion emission spectroscopy such as x-ray photoelectron spectroscopy and secondary ion mass spectroscopy, and more particularly to control of surface potential of insulating specimens being subjected to such spectroscopy.

BACKGROUND

In an x-ray photoelectron spectroscopic (XPS) instrument, a beam of x-rays illuminates a portion of a specimen to cause electrons to be emitted, for example as disclosed in U.S. Pat. No. 5,315,113 (Larson et al.). These emissions are analyzed with an energy analyzer to determine the composition of the surface. However, with an insulating specimen, the electron emissions leave the surface positively charged in the region of the x-ray illumination. The positive charge varies across the surface, thereby affecting the emitted electron energies and trajectories, and introducing errors into corresponding analyses.

In secondary ion mass spectroscopy (SIMS) a surface is irradiated with positive ions so as to cause emission of atoms and ions from the surface. The incident ions cause a buildup of positive charge on an insulating specimen. As for XPS, such a charge introduces errors into analyses.

Various approaches to these problems include, at least for XPS, interposing a grid close to the sample to smooth gradients in electrical potential, such as disclosed in U.S. Pat. No. 4,680,467 (Bryson). This introduces an interfering element and has limited applicability.

In another approach, the specimen is neutralized by flooding with low energy electrons. This provides a significant improvement, but generally results in non-uniform neutralization because an area larger than the region of photoemission is flooded, thereby supplying excess negative charge in the area outside of the photoelectron region. U.S. Pat. No. 5,432,345 ("Kelly patent", assigned to the present assignee) discloses smoothing the field gradients by discharging excess negative charge with irradiation of ultraviolet light or a beam of positive ions. This technique with radiation or ions can reduce the gradients quite significantly, but there remains some gradient with resulting effects on analyses. Also, the Kelly reference is directed primarily to ultraviolet radiation and gives few details in the use of positive ions. Ion sources are normally used for sputtering and the like, and typically produce ions with energies greater than 10 eV, although lower energy devices have been used experimentally.

A general problem with existing XPS instruments, even utilizing electron flooding, is sensitivity to neutralizer operating conditions. It has been difficult to obtain reproducible photoelectron peak positions and peak shapes.

SUMMARY

An object of the invention is to effect a substantially uniform surface potential on an insulating specimen in an x-ray photoelectron or a secondary ion emission instrument in which the specimen has an irradiation region receptive of an energy beam to effect an emission from the specimen so as to cause positive charging of the irradiation region. Another object is to provide the substantially uniform surface potential with any remnant of gradient even less than provided by the aforementioned background art.

The foregoing and other objects are achieved, at least in part, in such an instrument with an apparatus that comprises an electron means for flooding an area of the specimen including the irradiation region with an electron beam of low energy electrons to neutralize the positive charging, such that the flooding causes negative charging of the flooding area outside of the irradiation region. The apparatus further comprises an ion means for directing positive ions onto at least a portion of the flooding area proximate the irradiation region to neutralize the negative charging in such portion.

According to one aspect of the invention, the electron means effects the electron beam with a low energy less than about 2 eV and an energy spread less than about 0.5 eV. In a preferable embodiment, the electron means comprises a thermionic electron emitter formed of an electron emitting material having a work function less than about 2 eV to effect the low energy of the electron beam.

According to another aspect, preferably in combination with the low energy electron beam, the ions substantially have a low ion energy less than 10 eV. In a further aspect, preferably in combination with the low energy electron beam and the low ion energy, the electron means is spaced at a distance from the specimen, the electron beam has a beam diameter at the specimen, and a ratio of the distance to the diameter is less than about 10.

DETAILED DESCRIPTION

Figure 1:
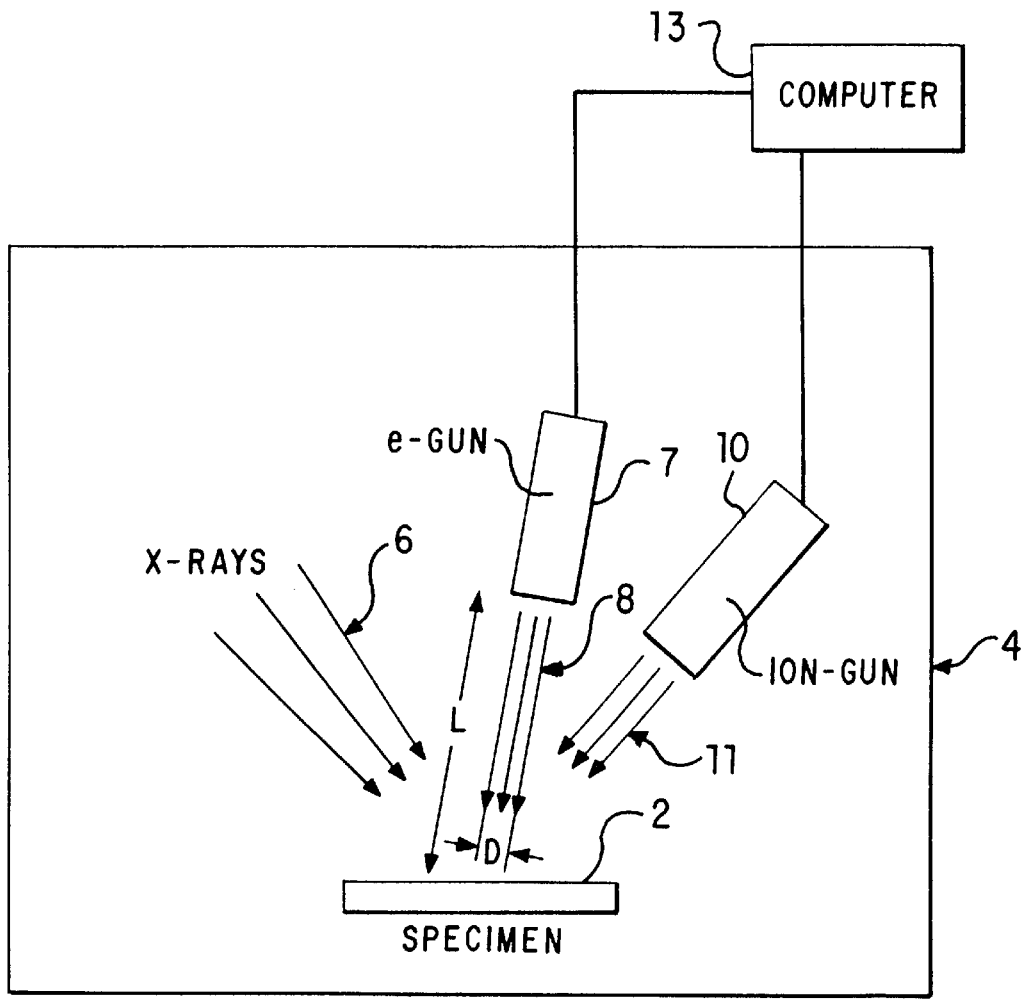
FIG. 1 is a schematic drawing illustrating an apparatus of the invention.

In one embodiment, an apparatus useful in the invention is utilized with an x-ray photoelectron (XPS) instrument for surface analysis, for example as disclosed in the aforementioned U.S. Pat. No. 5,513,113 ("Larson patent") incorporated herein by reference in its entirety. An insulating specimen 2 (FIG. 1) is mounted in the vacuum chamber of an XPS instrument 4. X-rays 6 are directed conventionally to the specimen where they illuminate an irradiation region or spot 12 (FIG. 2) on the specimen to emit photoelectrons (not shown). An electron gun 7 emits low energy electrons 8 which flood the specimen. A source 10 of charged particles directs a beam of positive ions 11 to the specimen. The electron gun and the ion source are controlled advantageously by a computer 13 that conveniently may be the same as the system computer such as described in the Larson patent.

The emission of photoelectrons from the specimen surface causes positive charging of the irradiation region 12. The area 14 flooded by the low energy electrons is generally larger than and includes the irradiation region, and thus neutralizes the positive charging but produces an excess of negative charge in the area outside the irradiation region. The ion beam 11 is directed onto at least a portion 16 of this area proximate the irradiation region to neutralize the negative charging. Although in this illustration the area of positive ions is shown to be larger than the electron flooded area 14, the ion beam may be directed to an area equal to or smaller than the flooded area, provided a significant area around the irradiated region is covered by the ion beam to effectively minimize potential gradients in and around the irradiated region. In a typical XPS spectrometer, the x-ray irradiation region 12 may have a diameter of 1 mm or smaller, the electron area 14 may have a diameter of 1 to 10 cm, and the ion area 16 may have a diameter of 10 to 50 cm.

Figure 3:
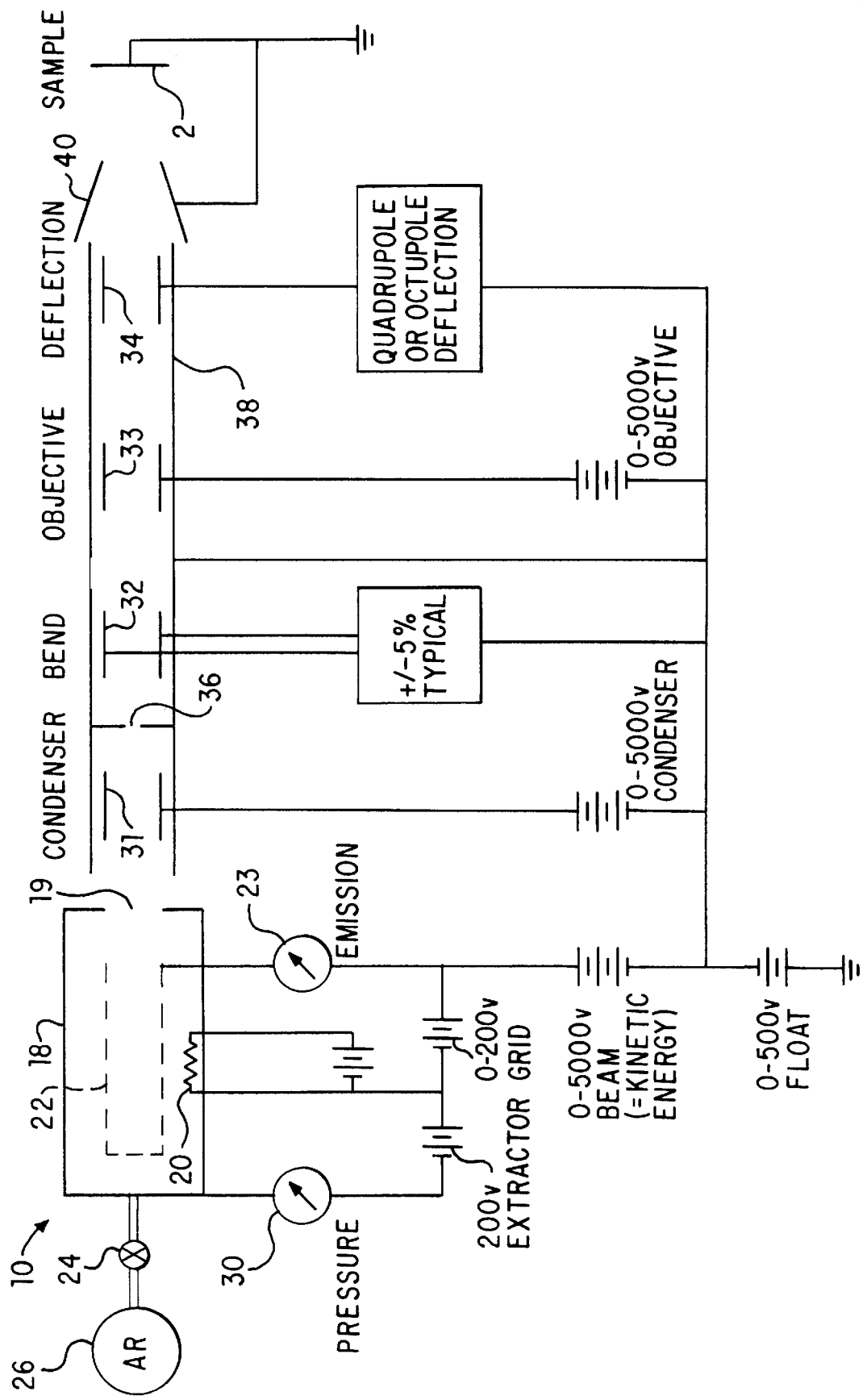
FIG. 3 is a schematic drawing of an ion gun utilized in the apparatus of FIG. 1.

According to one embodiment of the present invention, the ions in the beam 11 are substantially with a low ion energy less than 10 eV. In a suitable ion gun 10 (FIG. 3), an ionization chamber 18 encloses a thermionic filament 20 emitting electrons that are accelerated by the positive potential of a tubular grid 22 to ionize argon gas therein. Emission current may be measured with an ammeter 23 to the grid. The gas has a regulated inlet 24 from a gas supply 26 to effect a chamber pressure of about 25 mPa. The pressure is detected by an ammeter 30 with the chamber 18 acting as an extractor electrode. In tandem after an opening 19 in the ionization chamber are a cylindrical condenser lens 31, an aperture 36, a pair of beam bending plates 32, a cylindrical objective lens 33 and, optionally for steering, a cylindrical set of quadrupole or octupole deflection plates 34. The tube 38 containing these elements is set at a relatively low float voltage. The ions are accelerated through the tube from the high voltage grid 22, and slowed down to the desired energy in passing into a grounded conical exit ring 40 and thence to the grounded specimen 2. The lens voltages track as a percentage of the beam voltage. There is a bend (not shown) of about 5° in the tube 38 at the location of the bending plates 32 so as to eliminate neutral atoms from the ion beam. Although the foregoing illustrates a suitable source of ions, any conventional or desired source of low energy ions that can be adapted into the instrument may be used.

Figure 4:
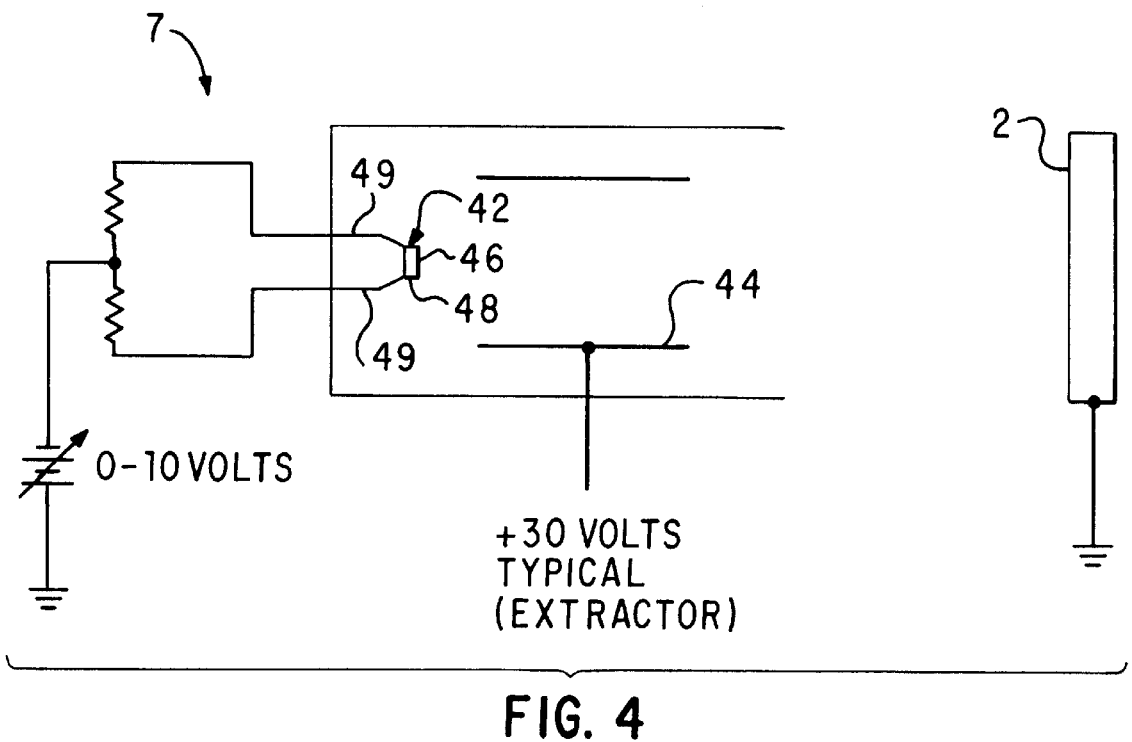
FIG. 4 is a schematic drawing of an electron gun utilized in the apparatus of FIG. 1.

According to another embodiment the flooding electrons have a relatively narrow spread of energy, the spread being substantially less than about 0.5 eV, for example about 0.3 eV. Also, preferably, the electrons have a very low energy, preferably less than 2 eV (compared with a spread of about 1 to 10 eV for conventional flooding). An electron gun 7 (FIG. 4) typically has a thermionic emitter 42 heated with an electrical current, with the emitted electrons being accelerated through a cylindrical extractor 44.

In a preferred means to achieve the desired energy spread, the emitter 42 is formed of an electron emitting material having a work function less than about 2 eV, for example 1 eV. For comparison, a conventional tungsten emitter has a work function of about 4.5 eV. With a low work function, the emitter is operated at lower temperature, thereby substantially reducing the width of the energy distribution and the fraction in the high energy tail of the Boltzman distribution. For example, the emitter may be formed of a film 46 of barium-strontium oxide on a platinum disk 48 heated by current in the supporting legs 49 welded to the disk. The film is similar to that previously formed on nickel cans utilized for emitters in vacuum tubes. A suitable emitter is a model ES-015 barium oxide disk cathode from Kimball Physics Inc., Wilton, N.H.

Figure 5:
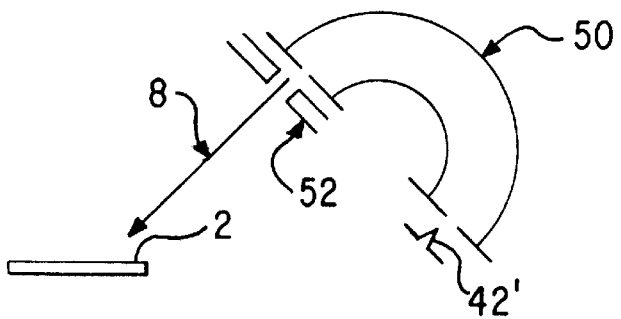
FIG. 5 is a schematic drawing of an embodiment with substitution of a source of electrons in FIG. 1 with a source incorporating an electron energy filter.

Alternatively the desired energy spread may be achieved with an electron energy filter such as a hemispherical electrostatic analyzer 50 (FIG. 5) disposed between the electron source, e.g. a thermionic emitter 42', and the specimen, with one or more intermediate lens 52 as needed. Such filter may be any electrostatic or electromagnetic energy analyzer configured for the present application, for example being a cylindrical electrostatic analyzer, or a hemispherical electrostatic analyzer (as shown) of the type disclosed in the Larson patent.

The maximum current of the flooding electrons at the specimen is limited by space charge proximate the specimen, the maximum being inversely proportional to the square of the ratio L/D of the distance L of the gun from the specimen to the diameter D of the flooding electron beam at the specimen. The diameter is generally about the same as that at the gun exit. To maximize this current, the electron gun should be as close as practical to the specimen. It was determined that the ratio L/D preferably should be less than about 10, more preferably less than about 6, where D is assumed to be the beam diameter at the gun exit.

It is particularly advantageous to utilize at least two and preferably all of the afore described embodiments in combination. Thus, in a preferred embodiment, the ion energies are substantially less than 10 eV, the flooding electrons have energies less than about 2 eV in a narrow energy spread of less than about 0.5 ev achieved with a low work function emitter, and the ratio of the electron gun distance to the beam diameter is less than about 10. More preferably the flooding electrons are effected with an electron emitter with a work function less than about 2 eV.

It has been found that the foregoing improvements effect a substantially more uniform potential than disclosed in the Kelly patent. Also, the instrument is significantly more robust and reliable than heretofore, in that a range of specimen types and surface areas can be analyzed without the previous variations in analytical results and sensitivity in setting electron flood current. The low electron energy and closer distance for the electron gun allow higher flooding current densities. Photoelectron density is up to about 40 nA/mm$^2$ for a focussed 10 micron diameter x-ray beam spot on an insulating specimen. It is desirable for the neutralizing electron current to be at least 10 time greater than the photoelectron current, and this can be achieved with the combined improvements allowing 400 nA/mm$^2$.

Figure 2:
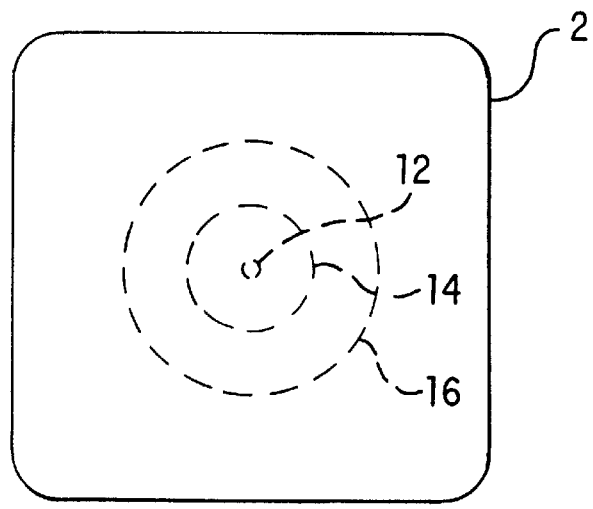
FIG. 2 shows the surface of a specimen of FIG. 1.

The invention may similarly be utilized beneficially for the neutralization of insulating specimens in other analytical instruments which effect positive charging of the specimen surface, for example in secondary ion mass spectroscopy (SIMS) in which a surface is irradiated with positive ions. The introduction of electron flooding and low energy positive ions is effected in substantially the same manner as for XPS. In FIG. 1, the x-rays 6 are replaced with a beam of positive ions (which are separate from the neutralizing beam of ions 11).

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. An apparatus for effecting a substantially uniform surface potential on an insulating specimen in an analytical instrument wherein the specimen has an irradiation region receptive of an energy beam to effect an emission from the specimen so as to cause positive charging of the irradiation region; the apparatus comprising:

electron means for flooding an area of the specimen including the irradiation region with an electron beam of low energy electrons to neutralize the positive charging, such that the flooding causes negative charging of the flooding area outside of the irradiation region; and ion means for directing positive ions onto at least a portion of the flooding area proximate the irradiation region to neutralize the negative charging in such portion;

wherein the electron means effects the electron beam with a low energy less than about 2 eV and an energy spread less than about 0.5 eV.

2. The apparatus of claim 1 wherein the electron means comprises an electron source and an electron energy filter disposed between the electron source and the specimen to effect the low energy of the electron beam.

3. The apparatus of claim 1 wherein the electron means comprises a thermionic electron emitter formed of an electron emitting material having a work function less than about 2 eV to effect the low energy of the electron beam.

4. The apparatus of claim 3 wherein the ions substantially have an ion energy less than 10 eV.

5. The apparatus of claim 4 wherein the electron means is spaced at a distance from the specimen, the electron beam has a beam diameter at the specimen, and a ratio of the distance to the diameter is less than about 10.

6. The apparatus of claim 5 wherein the energy beam is an x-ray beam to effect emission of photoelectrons so as to cause the positive charging.

7. The apparatus of claim 3 wherein the electron means is spaced at a distance from the specimen, the electron beam has a beam diameter at the specimen, and a ratio of the distance to the diameter is less than about 10.

8. The apparatus of claim 3 wherein the electron emitter comprises a barium oxide based cathode.

9. The apparatus of claim 1 wherein the ions have an ion energy less than 10 eV.

10. The apparatus of claim 5 wherein the electron means is spaced at a distance from the specimen, the electron beam has a beam diameter at the specimen, and a ratio of the distance to the diameter is less than about 10.

11. The apparatus of claim 1 wherein the electron means is spaced at a distance from the specimen, the electron beam has a beam diameter at the specimen, and a ratio of the distance to the diameter is less than about 10.

12. The apparatus of claim 1 wherein the energy beam is an x-ray beam to effect emission of photoelectrons so as to cause the positive charging.

13. The apparatus of claim 1 wherein the energy beam is a beam of positive ions so as to cause the positive charging.

14. An apparatus for effecting a substantially uniform surface potential on an insulating specimen in an analytical instrument wherein the specimen has an irradiation region receptive of an energy beam to effect an emission from the specimen so as to cause positive charging of the irradiation region; the apparatus comprising:

electron means for flooding an area of the specimen including the irradiation region with an electron beam of low energy electrons to neutralize the positive charging, such that the flooding causes negative charging of the flooding area outside of the irradiation region; and ion means for directing positive ions onto at least a portion of the flooding area proximate the irradiation region to neutralize the negative charging in such portion, wherein the ions have an ion energy less than 10 eV.

15. The apparatus of claim 14 wherein the electron means is spaced at a distance from the specimen, the electron beam has a beam diameter at the specimen, and a ratio of the distance to the diameter is less than about 10.

16. The apparatus of claim 14 wherein the energy beam is an x-ray beam to effect emission of photoelectrons so as to cause the positive charging.

17. The apparatus of claim 14 wherein the energy beam is a beam of positive ions so as to cause the positive charging.

18. An apparatus for effecting a substantially uniform surface potential on an insulating specimen in an analytical instrument wherein the specimen has an irradiation region receptive of an energy beam to effect an emission from the specimen so as to cause positive charging of the irradiation region; the apparatus comprising:

electron means for flooding an area of the specimen including the irradiation region with an electron beam of low energy electrons to neutralize the positive charging, such that the flooding causes negative charging of the flooding area outside of the irradiation region; and ion means for directing positive ions onto at least a portion of the flooding area proximate the irradiation region to neutralize the negative charging in such portion;

wherein the electron means is spaced at a distance from the specimen, the electron beam has a beam diameter at the specimen, and a ratio of the distance to the diameter is less than about 10.

19. The apparatus of claim 18 wherein the energy beam is an x-ray beam to effect emission of photoelectrons so as to cause the positive charging.

20. The apparatus of claim 18 wherein the energy beam is a beam of positive ions so as to cause the positive charging.

* * * * *

UNITED STATES PATENT AND TRADEMARK OFFICE
CERTIFICATE OF CORRECTION

PATENT NO.: 5,990,476
DATED: November 23, 1999
INVENTOR(S): Larson et al.

It is certified that error appears in the above-identified patent and that said Letters Patent is hereby corrected as shown below:

Column 5, line 33 in claim 10, please delete "5" and insert --9--.

Signed and Sealed this

First Day of May, 2001

Attest:

NICHOLAS P. GODICI

Attesting Officer

Acting Director of the United States Patent and Trademark Office